United States Patent [19]

Wagenknecht, deceased et al.

[11] 4,156,716

[45] May 29, 1979

[54] PLAQUE INHIBITING COMPOSITION AND METHOD

[75] Inventors: Austin C. Wagenknecht, deceased, late of Hennepin County, Minn., by Don Austin Wagenknecht, personal representative; George V. Daravingas, Edina; William E. Koski, Minneapolis, both of Minn.

[73] Assignee: General Mills, Inc., Minneapolis, Minn.

[21] Appl. No.: 855,126

[22] Filed: Nov. 28, 1977

[51] Int. Cl.$^2$ .......................... A61K 7/16; A61K 9/68
[52] U.S. Cl. ........................................ 424/48; 424/49; 426/3
[58] Field of Search .................... 424/48–58; 426/3–6

[56] References Cited

U.S. PATENT DOCUMENTS

| 2,366,589 | 1/1945 | Borglin | 426/3 X |
| 2,744,049 | 1/1956 | Salzmann | 424/49 X |
| 3,655,866 | 4/1972 | Bilotti | 424/48 |
| 3,818,107 | 6/1974 | Yolles | 426/3 |
| 3,821,417 | 6/1974 | Westall et al. | 426/3 |
| 3,899,593 | 8/1975 | Hammond et al. | 426/3 |
| 3,914,434 | 10/1975 | Bohni | 424/343 |
| 3,930,026 | 12/1975 | Clark | 426/3 |
| 3,973,041 | 8/1976 | Du Ross | 426/3 |
| 4,000,320 | 12/1976 | Klose et al. | 426/3 |
| 4,022,880 | 5/1977 | Vinson et al. | 424/49 |

FOREIGN PATENT DOCUMENTS

| 959764 | 12/1974 | Canada. |
| 1290627 | 9/1972 | United Kingdom. |
| 1296952 | 11/1972 | United Kingdom. |
| 1372932 | 11/1974 | United Kingdom. |

Primary Examiner—Shep K. Rose
Attorney, Agent, or Firm—Gene O. Enockson; John A. O'Toole

[57] ABSTRACT

This invention discloses compositions effective in inhibiting or reducing plaque in the oral cavity. Chewing gums are a preferred vehicle for delivering the plaque inhibiting benefit of the present invention.

11 Claims, No Drawings

PLAQUE INHIBITING COMPOSITION AND METHOD

BACKGROUND OF THE INVENTION

1. Field of the Invention

This invention relates to the practice of dental hygiene, and in particular, to the removal of, or the inhibition of the growth of plaque in the oral cavity.

2. Description of the Art

The following references, while not exhaustive discuss various materials which are included in compositions which contact the oral cavity. Salzmann, in U.S. Pat. No. 2,744,049 issued May 1, 1956, discusses dental creams containing a partial ester of glycerine and a higher fatty acid material. The Salzmann patent also discusses the use of dicalcium phosphate dihydrate as an abrasive, and as well the use of sodium lauryl sulfate. U.S. Pat. No. 3,622,662 issued to Roberts et al, Nov. 23, 1971, describes dental creams which may contain various zinc salts or sodium lauryl sulfate and compositions which may be flavored with peppermint, spearmint or clove oils.

Clark, in U.S. Pat. No. 3,930,026 issued Dec. 30, 1975, describes the enhancement of flavor in chewing gums obtained by sorbing the flavoring onto a hydrophilic colloid in conjunction with a surfactant. Among the surfactants disclosed are anionic materials, including sodium di(2-ethylhexyl)sulfosuccinate. Clark also states that nonionic surfactants may be used to sorb the flavor into the gum including fatty acid monoglycerides or fatty acid diglycerides. British Pat. No. 1,290,627 in the name of Pader, published Sept. 27, 1972, describes mouthwashes, having activity against calculus and plaque, containing zinc salts and further describing the use of sodium lauryl sulfate to provide foaming action.

British Pat. No. 1,296,952 reported by Cancro et al and published Nov. 22, 1972, states that plaque and calculus may be diminished by zinc phenolsulphonate and certain enzymes in dentifrice compositions. The Cancro patent also describes the use of certain abrasives, buffering agents, and various surfactants. British Pat. No. 1,372,932 published Nov. 6, 1974, describes purported anticaries compositions including chewing gums, dentifrices and candylike products. In particular, the aforementioned British patent states that stearoyl-2-lactylate has been found effective to inhibit the production of dextran in the mouth.

Canadian Pat. No. 959,764 issued Dec. 24, 1974, to Pader, describes dentifrice compositions containing a source of zinc ions and various enzymes. Pader also describes various surfactants which may be included in toothpastes, including sodium lauryl sulfate and dioctyl sodium sulfosuccinate.

U.S. Pat. No. 4,022,880 issued to Vinson et al, on May 10, 1977, describes compositions for inhibiting dental plaque containing a source of zinc ions and a halosalicylanilide, a quaternary ammonium compound and other specified materials. The Vinson et al patent also states that sodium lauryl sulfate and polishing agents may be used in the compositions. Hass in Ser. No. 124,465, filed Mar. 15, 1971 discloses that stearoyl-2-lactylate may be used to prevent the formation of dextran in the mouth.

Yolles, in U.S. Pat. No. 3,818,107 issued June 18, 1974, describes chewing gums which incorporate the flavor in a polymeric backbone. Yolles states that the flavor release in the chewing gum is sustained by the molecular arrangement of the flavor group. In U.S. Pat. No. 3,651,206 issued to Litchfield et al on Mar. 21, 1972, are described chewing gums containing various aliphatic aldehydes as anticaries agents. Various oral preparations for preventing dental plaque are described in U.S. Pat. No. 3,940,476 issued Feb. 24, 1976 to Hass. Comollo states in U.S. Pat. No. 3,984,574 issued Oct. 5, 1976 that non-tacky chewing gums may be made containing mono- and diglycerides of fatty acids in an amount up to ten percent (10%) by weight of the base composition.

U.S. Pat. No. 3,821,417 issued to Westall et al on June 28, 1974, describes the use of dihydrochalcone in chewing gums. This patent further describes the use of butylated hydroxyanisole, butylated hydroxytoluene and propyl gallate as antioxidants in chewing gums. DuRoss, in U.S. Pat. No. 3,973,041 issued Aug. 3, 1976 describes the use of sorbitol powder, butylated hydroxyanisole, and glycerine in chewing gums. Additional disclosures of sorbitol as well as other sugars, such as xylitol, are made in various United States Patents including: U.S. Pat. No. 4,000,320 issued to Klose et al on Dec. 28, 1976; U.S. Pat. No. 3,899,593 issued to Hammond et al on Aug. 12, 1975; U.S. Pat. No. 3,914,434 issued Oct. 21, 1975 to Bohni; U.S. Pat. No. 3,296,079 issued Jan. 3, 1967 to Griffin; and U.S. Pat. No. 3,655,866 issued Apr. 11, 1972 to Billoti.

Dental plaque is a deposit which accummulates on the teeth and adjacent surfaces in the oral cavity. The plaque is a product of microbial growth, primarily derived from food residues in the mouth. Mucoproteins and minerals present from the saliva and dead cells in the mouth also assist in plaque formation.

Plaque is removed to some extent by effective brushing of the teeth, but the less accessible and more sheltered areas of the mouth which cannot be readily reached by a toothbrush, are particularly susceptible to plaque and eventually, calculus growth. Left unhindered, the plaque increases in size and more tenaciously adheres to the teeth. The bacterial metabolism within the plaque on the tooth surface results in the production of acids, toxins and enzymes which are deleterious to the neighboring oral tissues. It has been stated that there is evidence pointing to plaque as being the direct cause of dental caries, due to the generation of acids within the plaque structure. In any event plaque is unsightly, and undesirable.

The present invention describes ingredients in compositions to retard and/or remove plaque from the surface of the teeth. It is also noted that when the plaque is removed or prevented from forming upon the teeth, that the potential growth of calculus is also advantageously limited.

The embodiments of the plaque inhibiting composition are described below in the summary of the invention.

Throughout the specification and claims, percentages and ratios are by weight, and temperatures are in degrees Celsius, unless otherwise indicated.

SUMMARY OF THE INVENTION

The present invention encompasses a composition for use in the oral cavity to moderate the incidence of dental plaque containing an effective amount of a mixture of di(2-ethylhexyl)sulfosuccinate salt and a zinc compound in a weight ratio of from about 1,000:1 to about 1:1,000.

The present invention in a solid form food product to moderate the incidence of dental plaque containing an effective amount of a di(2-ethylhexyl)sulfosuccinate salt and zinc compound in a weight ratio of from about 1,000:1 to about 1:1,000.

The present invention in a chewing gum comprising:
(a) from about 10% to about 95% by weight of a gum base; and,
(b) from about 0.001% to about 20% by weight of a mixture of a di(2-ethylhexyl)sulfosuccinate salt and a zinc compound in a weight ratio of from about 1,000:1 to about 1:1,000.

DETAILED DESCRIPTION OF THE INVENTION

As shown in the summary of the invention, the plaque inhibiting compositions of the present invention may take several forms. That is, the present invention is concerned with the application of the compositions described herein to the oral cavity and are not limited to any particular vehicle, although certain preferred forms of the composition are enumerated.

Broadly stated, the present invention embraces mouthwashes, toothpastes, toothpowders and other dental applications such as painting of the composition onto the tooth surface. In the food product line, the present invention envisages all forms of liquid and dry foods, including soft drinks, cocoa powders, and dairy products such as milk supplemented with the compositions of the present invention. Snack foods such as potato chips, cheese curls, candies in both hard and soft form including chocolates, mints, troches, lozenges, chewable stick candy and the like are also utilized. Of particular interest in the present invention are all forms of chewing gum which provide an excellent delivery system for the compositions of the present invention.

Chewing gums include those with natural and synthetic bases as described below and are also inclusive of bubble gum. Chewing gum is a preferred vehicle for delivering the compositions of the present invention because, due to the inherent nature of chewing gum, a prolonged period of contact with the oral cavity is reached. Moreover, the gum base can provide for sustained release of the active components of the present invention, thus minimizing the amount of the active components which must be used.

As used in the present invention the term effective amount of the composition is used synonymously with the term sufficient amount, both terms referring to the amount of the composition required to achieve plaque reduction or inhibition. There is not set definition for the amount of the composition required to achieve the desired plaque inhibition. That is, the in use concentration of the various components of the composition will depend upon the manner of application to the oral cavity. Specifically, if the compositions of the present invention are utilized as a mouthwash a much larger amount or a longer duration of the use of the composition should be employed as compared to a painting of the composition onto the teeth by a dental technician.

In the preferred aspect of the present invention, namely the chewing gum, the examples herein give guidelines to the use of the components of the present invention to provide effective plaque inhibition. Similarly, it can be seen that for toothpastes, mints, troches, lozenges, and mouthwashes that the manner of using each formulation is to be determined by considering the amount of the composition normally utilized by the individual and the duration that the composition is present in the oral cavity.

The di(2-ethylhexyl)sulfosuccinate salt, as used in the present invention, is also known in the art as DSS or dioctyl sulfosuccinate. The foregoing terms are used equivalently in the specification and claims of this application.

The di(2-ethylhexyl)sulfosuccinate salt is conveniently used at a level from about 0.001% to about 15% by weight of the composition. In its more preferred aspects of the present invention, the composition contains the di(2-ethylhexyl)sulfosuccinate salt at from about 0.005% to about 5%, preferably from about 0.01% to about 3% by weight.

The zinc compound is utilized to supply a source of zinc ions to the oral cavity. The zinc compound as previously stated, is utilized at a level of from about 0.001% to about 5%, preferably from about 0.005% to about 3%, and most preferably from about 0.01% to about 2% by weight.

The foregoing amounts of the zinc compound are sufficient to provide a level of about 50 parts per million of zinc ion. Preferably, the composition is formulated such that greater than 75 parts per million and most preferably greater than 130 parts per million of the zinc ion is available from the composition.

The zinc ompound is not limited to any one source of zinc ions. For instance, suitable salts which supply zinc ions include the phosphates, sulfates, chlorides, fluorides, oxides and zinc fatty acids. Of particular interest are zinc phenolsulfonate, zinc oxide and the stearic acid salt of zinc. The last mentioned component is particularly useful in that it also serves a lubricant function which is desirable when forming tablets such as for the mint or hard candy variation of the present invention.

In the present invention the weight ratio of the di(2-ethylhexyl)sulfosuccinate salt to the zinc compound is at from about 1,000:1 to about 1:1,000, preferably from about 250:1 to 1:250, and most preferably from about 20:1 to about 1:20.

The chewing gum aspect of the present invention utilizes the mixture of the di(2-ethylhexyl)sulfosuccinate salt and the zinc compound at a level from about 0.001% to about 20%, preferably from about 0.001% to about 10%, and most preferably from about 0.001% to about 3% by weight of the chewing gum.

In the present invention it is also contemplated that various commercially available flavors may be utilized to enhance the sensory effect of the composition. In particular, essential oils including but not limited to cinnamon oil, peppermint oil, and spearmint oil, as well as mixtures thereof may be included at conventional levels in the compositions of the present invention.

Where the term salt is employed in the present invention the cation may be any material which is accepted as safe for food or chewing gum uses. Preferably the cations are selected from a group consisting of sodium, potassium, calcium, magnesium, ammonium, and substituted ammonium and mixtures thereof. The sodium salt is most preferred in the present invention both from a cost and a solubility standpoint followed by the calcium and magnesium salts. Where additional germicidal effect is desired the ammonium or substituted ammonium salts are particularly valuable.

The present invention is particularly concerned with the use of chewing gums as a means for delivering anti-plaque compositions. First, chewing gums are ordinarily used such that prolonged contact with the surface of the teeth and gums is obtained. Secondly, the mastication or chewing of the gum aids in cleaning or hindering the ability of plaque to tightly adhere to the teeth. In chewing gums, a gum base is a necessary component.

All manner of natural or synthetic gum bases are to be considered as included within the scope of the present invention. Examples of suitable gum bases include chicle, gutta percha, jelutong, balata, namaquland rubber, almeidana gum, abba rubber, gutta siak, gutta cotie, gutta kay, gutta hangkang, gutta jangkar, gutta sundik, gutta soh, gutta susu, gutta penang, and yellow gutta. Further examples of gum bases include rosins, such as cumarone resin, pontianak resin, copal gum, kauri gum, dammar gum, sweet bay gum, spruce gum, and balsams. Moreover, suitable gum bases include crown gum, nispero, rosidinha, pendare, perillo, niger gutta, and tuno.

Additional chewing gum base materials include elastimers such as polyisobutylene, polyisoprene, isobutylene-isoprene copolymers and copolymers of butadiene and styrene, hydrogenated or partially hydrogenated vegetable oils such as soy bean, cotton seed, corn, peanut, and palm or animal fats such as tallow and lard. In addition paraffin, beeswax, petroleum wax, polyethylenes, and polyvinylacetates may be employed. Further descriptions of suitable chewing gum bases are found in U.S. Pat. No. 2,366,589 issued to Borglin Jan. 2, 1945; U.S. Pat. No. 3,821,417, issued to Westall, et al on June 28, 1974; U.S. Pat. No. 4,041,179 issued to Stubits et al on Aug. 9, 1977; and U.S. Pat. No. 3,984,574 issued to Comollo on Oct. 5, 1976; all of which are herein incorporated by reference.

The amount of the gum base utilized in the chewing gum aspect of the present invention is from about 10% to about 95%, preferably from about 15% to about 70% by weight of the chewing gum composition.

While no sweetener is required in the present invention, it is desired that the product be appetizing to consumers. Thus, any form of natural or synthetic sweetener may be included in the present invention. It is preferred, however, that sucrose, fructose, and glucose content of the compositions be restricted or eliminated due to the fact that these materials provide "food" from which plaque may be formed. Artificial sweeteners such as saccharin, cyclamates, and dihydrochalcones may be included at conventional amounts in the compositions of the present invention.

A preferred source of sweetening agents for the present invention are members selected from the group consisting of xylitol, sorbitol, and mannitol as well as mixtures thereof. The foregoing polyol sugars are generally utilized at from about 5% to about 80%, preferably from about 10% to about 70% by weight of the composition. The particularly preferred polyol sugar is xylitol which is reported to have anti-cariogenic benefits. The use of xylitol in various products such as chewing gums is reported in U.S. Pat. No. 3,296,079 to Griffin, issued Jan. 3, 1967; U.S. Pat. No. 3,655,866, issued to Bilotti on Apr. 11, 1972; U.S. Pat. No. 3,914,434 issued to Bohni on Oct. 21, 1975; U.S. Pat. No. 4,000,320 issued to Klose, et al on Dec. 28, 1976 and U.S. Pat. No. 3,899,593 issued to Hammond, et al on Aug. 12, 1975, all of which are herein incorporated by reference.

A component which may be included in the present invention is an alkaline buffer which serves to raise or maintain the pH in the oral cavity. The term alkaline buffer is not meant to imply that the pH in the oral cavity must be within the alkaline range but rather than it is preferred that the pH of the oral cavity be in the alkaline range. In fact, the buffering capacity should be such that the pH of the oral cavity is maintained at from about 5.5 to about 10, most preferably from about 6 to about 9. Any alkaline buffer or combinations of alkaline buffers which provide the desired effect may be used. Prominently noted, is the use of bicarbonates particularly sodium bicarbonate to provide the desired pH effect. Other buffers which may be used include carbonates, sesquicarbonates, citrates, and polyphosphates including pyrophosphates, orthophosphates, tripolyphosphates, and hexametaphosphate.

The amount of buffer which is required will, of course, depend upon the acidic nature of the composition in which it is being used. It is generally found that employing the buffer at from about 1% to about 30% by weight of the composition ensures that the desired pH range in the oral cavity will be met. Preferably the amount of the alkaline buffer employed is from about 2% to about 20% by weight of the composition.

Another component which is desirably used in the present invention is a dental abrasive. Dental abrasives are particularly valuable in chewing gums due to the polishing action which occurs during mastication. The term dental abrasive includes all manner and form of such materials which are normally used in toothpaste, chewing gums, and the like. Specifically dicalcium diphosphate dihydrate is the preferred dental abrasive of the present invention. This particular material also serves to function as an alkaline buffer as described above. The use of dicalcium phosphate and its dihydrate powder are described in U.S. Pat. Nos. 3,011,949 and 3,655,866, issued respectively Dec. 5, 1961 and Apr. 11, 1972 to Bilotti, both of which are herein incorporated by reference.

Further dental abrasives which may be utilized in the present invention include calcium carbonate, sodium metaphosphate, aluminum hydroxide, magnesium carbonate, calcium sulphate, silicas including aerogels and xerogels, and tricalcium phosphate. Expanded disclosures of dental abrasives suitable fur use in the present invention are found in U.S. Pat. No. 2,744,049, issued May 1, 1956 to Salzmann, et al, herein incorporated by reference. The amount of the dental abrasive employed in the present invention is generally within the range of from about 1% to 30%, preferably from about 1.5% to about 20% by weight.

Yet another desirable ingredient in the composition of the present invention is the use of glycerine. In the chewing gum aspect of the present invention glycerine serves to soften and maintain the chewability of the chewing gum for prolonged periods. The glycerine also adds to the sweetness of the composition. The glycerine is ordinarily added at levels of from about 0.01% to about 10%, preferably at from about 0.2% to about 5% by weight of the composition.

The present invention includes as optional components water or a monohydric alcohol at from about 2% to about 99%, preferably at from about 5% to about 70%, and most preferably from about 10% to about 50% by weight of the composition. It is of course recognized that it is particularly valuable to use mixtures of water and the monohydric alcohol generally within the weight ratio of from about 20:1 to about 1:20, preferably from about 10:1 to about 1:10.

The preferred monohydric alcohols are methanol, ethanol, or isopropanol although other monohydric alcohols generally including those having up to 18 carbon atoms may be utilized in the present invention. The preferred monohydric alcohol is ethanol. It should be recognized that where the product will be ingested that only ethanol should be used.

In vitro testing to determine the effectiveness of the compositions of the present invention is conducted in accordance with the accepted practices of determining plaque formation. For some of the general aspects of in vitro testing not discussed below, see "An In Vitro Method For Assessing the Plaque Forming Ability of Oral Bacteria," authored by McCabe et al reported in the ARCHIVES OR ORAL BIOLOGY, Volume 12, pages 1653-1656, 1967; and Effect of Microbial Interactions on In Vitro Plaque Formation by Streptococcus Mutans, by Miller et al reported in the JOURNAL OF DENTAL RESEARCH, March-April 1974, Volume 53, No. 2, pages 427-434, both of which are herein incorporated by reference.

The streptococcus mutans used in the experiment was strain 6715, in a 3% trypticase-soy broth, plus 5% sucrose. The streptococcus mutans was innoculated into 10 milliliters of sterile broth in a 20×150mm test tube. Sterile 20 gauge nichrome steel wires, 150mm long and mounted in No. 2 rubber stoppers, were suspended in the media and incubated for 24 hours at 37 degrees Celsius. For 5 consecutive days, the wires were transferred into freshly reinoculated tubes of sterile media. They were then transferred through uninnoculated media for 5 more days. In each instance, the wires protruded 37-38mm below the surface of the medium. At the end of the 10 day period, the portion of the wire containing the bacterial (plaque) deposit is cut off and placed in a preweighed aluminum pan and dried to a constant weight at 70 degrees Celsius. The dry weight of the plaque is then established by burning off the plaque deposit in an open flame and reweighing the clean, dry wire. Blank samples of the wire were found not to lose any weight due to the open flame treatment.

To determine the extent of plaque growth in the presence of the compositions of the present invention, the foregoing procedure was followed with the exception of the introduction of the various components of the invention at stated levels. Inactive components, such as gum base, were not included in each test conducted, due to the difficulty in handling the test medium solutions. That is, where gum base is present in the test tube, it is difficult to avoid having some of the gum base adhere to the nichrome wire, thus giving false readings in the determination of the plaque. The gum bases and other inactive components of the present invention were, however, separately determined to have minimal effect on plaque growth.

In vivo testing is conducted with human volunteers, using a fully constituted product, containing the active plaque inhibiting portion of the composition and the inert ingredients. In particular, for the testing of the chewing gums, a group of 20 volunteers is divided in random fashion into 2 groups of 10 each. During the first week, one group will chew a controlled gum which is available on the market, while the second group uses a gum in accordance with the present invention. In the second week, regular oral hygiene will be followed by all subjects in the test. This is to ensure that all volunteers who are known to readily form plaque will not develop gingivitis or any other oral condition, which would affect their health or the test scores. During the third week, the groups are switched, such that the group which previously used the controlled gum will now use the gum made in accordance with the present invention and vice versa.

To demonstrate the effectiveness of the present invention, only a limited amount of chewing gum and chewing time by the subjects is allowed. Further, to demonstrate the effectiveness of the compositions of the present invention, the testing is conducted such that the subjects only chew the gum on one side of the mouth during the entire test. During the test period, the volunteers chew their assigned gum, once in the morning and once in the later afternoon for 10 minutes on the right side of the mouth only, under supervision, to ensure that the instructions are followed fully. An additional stick of gum is given to each volunteer to chew for 10 minutes before going to bed. This test is also conducted such that the gum is chewed only on the right side of the mouth. On the last day of the test period, intra-oral photographic records of the unstained anterior areas of the mouth are made. Any gingivitis and dental plaque will be estimated and recorded, according to accepted scientific principles.

To further ensure that the compositions of the present invention are effective even in the absence of mastication, that is, a high degree of chewing which alone is known to have some cleaning benefits to the teeth, additional in vitro testing is conducted. In this test, freshly extracted human teeth were treated 3 times daily with a fresh human saliva solution. The teeth received 3 ten minute treatments at zero, three and six hour intervals each day, followed by incubation overnight. The tests were variously conducted for one or two days to determine the initial buildup of plaque in the control and test solutions. As described earlier the compositions of the present invention omitted inert ingredients which were not essential. The amount of plaque buildup on the teeth is determined by the difference in the optical density of the freshly extracted teeth and the teeth following the period of treatment in the saliva with and without the compositions of the invention present. In general, as noted in the examples, the foregoing series of 3 tests, indicates a high degree of effectiveness of the compositions of the present invention over the control.

EXAMPLE I

A plaque inhibiting gum is prepared according to the present invention by mixing the following components and pressing the mixture into 3 gram sticks:

| | |
|---|---|
| gum base - Palojo L. A. Dreyfus | 25% |
| xylitol | 10% |
| sodium bicarbonate | 2% |
| sorbitol | 35% |
| Sorbo (70% sorbitol in H2O) | 15% |
| dicalcium phosphate dihydrate | 5% |
| mannitol | 5% |
| glycerine | 0.5% |
| zinc oxide | 0.8% |
| sodium di(2-ethylhexyl)sulfosuccinate | 0.8% |
| balance flavor and coloring | q.s. |

The chewing gum when tested as previously described is found effective in removing plaque from the surface of the teeth and in inhibiting the growth of new plaque.

In use it is suggested that the chewing gum be masticated as single sticks at least twice a day for a period of ten minutes each time for maximum effectiveness.

EXAMPLE II

Plaque inhibiting mints in hard form weighing 5 grams are prepared containing the following ingredients:

| | |
|---|---|
| xylitol | 10% |
| sodium bicarbonate | 2% |
| sorbitol | 65% |
| Sorbo (70% sorbitol in H2O) | 15% |
| mannitol | 5% |
| glycerine | 0.5% |
| zinc oxide | 0.8% |
| sodium di(2-ethylhexyl)sulfosuccinate | 0.8% |
| balance flavor and coloring | q.s. |

The plaque inhibiting mint when used as previously described is found to be effective in inhibiting plaque formation on the surface of the teeth. The mint form of the present invention is preferably used after each meal by sucking on the mint for a period of five minutes.

EXAMPLE III

A plaque inhibiting mouthwash is prepared by combining a mixture containing:

| | |
|---|---|
| water | 85% |
| ethanol | 10% |
| sodium bicarbonate | 2% |
| zinc oxide | 0.8% |
| sodium di(2-ethylhexyl)sulfosuccinate | 0.8% |
| balance flavor and coloring | q.s. |

The mouthwash is tested as previously described and found to be plaque inhibiting. Suggested usage for the mouthwash, involves swishing 50 ml of the product in the mouth after each meal for a period of five minutes.

What is claimed is:

1. A chewing gum comprising:
   (a) from about 10% to about 95% by weight of a gum base; and,
   (b) from about 0.001% to about 20% by weight of a mixture of a di(2-ethylhexyl)sulfosuccinate salt and a zinc compound in a weight ratio of from about 1,000:1 to about 1:1,000.

2. The chewing gum of claim 1 containing from about 0.005% to about 5% by weight of the di(2-ethylhexyl)sulfosuccinate salt.

3. The chewing gum of claim 2 containing from about 0.01% to about 3% by weight of the di(2-ethylhexyl)sulfosuccinate salt.

4. The chewing gum of claim 3 containing from about 0.01% to about 2% by weight of the zinc compound.

5. The chewing gum of claim 4 containing from about 0.02% to about 3% by weight of the zinc compound.

6. The chewing gum of claim 5 containing a flavor selected from the group consisting of cinnamon oil, peppermint oil, and spearmint oil and mixtures thereof.

7. The chewing gum of claim 6 wherein the flavor is cinnamon oil.

8. The chewing gum of claim 7 containing from about 0.01% to about 10% by weight of glycerine.

9. The chewing gum of claim 8 containing from about 5% to about 80% by weight of a member selected from the group consisting of xylitol, sorbitol, and mannitol and mixtures thereof.

10. The chewing gum of claim 9 containing from about 1% to about 30% by weight of a member selected from the group consisting of dental abrasives and alkaline buffers and mixtures thereof.

11. The chewing gum of claim 10 wherein the cation of the salt is selected from the group consisting of sodium, potassium, calcium, magnesium, ammonium, and substituted ammonium and mixtures thereof.

* * * * *